(12) United States Patent
Clark

(10) Patent No.: US 10,912,759 B2
(45) Date of Patent: Feb. 9, 2021

(54) **TOPICAL GEL COMPOSITIONS FOR THE TREATMENT OF *STAPHYLOCOCCAL* INFECTIONS**

(71) Applicant: William Andrew Clark, Johnson City, TN (US)

(72) Inventor: William Andrew Clark, Johnson City, TN (US)

(*) Notice: Subject to any disclaimer, the term of this patent is extended or adjusted under 35 U.S.C. 154(b) by 0 days.

(21) Appl. No.: 16/415,239

(22) Filed: May 17, 2019

(65) Prior Publication Data

US 2019/0350896 A1 Nov. 21, 2019

Related U.S. Application Data

(60) Provisional application No. 62/672,608, filed on May 17, 2018.

(51) Int. Cl.

| | | |
|---|---|---|
| *A61K 31/355* | (2006.01) | |
| *A61K 9/00* | (2006.01) | |
| *A61K 9/06* | (2006.01) | |
| *A61K 31/375* | (2006.01) | |
| *A61K 47/60* | (2017.01) | |
| *A61K 31/01* | (2006.01) | |
| *A61K 36/53* | (2006.01) | |
| *A61P 31/04* | (2006.01) | |
| *A61K 47/54* | (2017.01) | |

(52) U.S. Cl.
CPC ......... *A61K 31/355* (2013.01); *A61K 9/0014* (2013.01); *A61K 9/06* (2013.01); *A61K 31/01* (2013.01); *A61K 31/375* (2013.01); *A61K 36/53* (2013.01); *A61K 47/547* (2017.08); *A61K 47/60* (2017.08); *A61P 31/04* (2018.01)

(58) Field of Classification Search
None
See application file for complete search history.

(56) References Cited

U.S. PATENT DOCUMENTS

| | | | |
|---|---|---|---|
| 7,790,190 B2 * | 9/2010 | Papas | A61K 31/355 424/400 |
| 2016/0206588 A1 * | 7/2016 | Berl | A23D 9/007 |
| 2018/0117168 A1 * | 5/2018 | Cole | A61K 31/519 |

OTHER PUBLICATIONS

O'Dowd H. et al. Discovery and Characterization of a Water Soluble Prodrug of a Dual Inhibitor of Bacterial DNA Gyrase and Topoisomerase IV. Medicinal Chemistry Letters 6(7)822-826, Jul. 2015. (Year: 2015).*

Bajaj A. et al. Self Nanoemulsifying Drug Delivery System of Cepodoxime Proxetil Containing Tocopherol Polyethylene Glycol Succinate. Drug Development and Industrial Pharmacy 39(5)635-645, May 2013. (Year: 2013).*

* cited by examiner

*Primary Examiner* — Ralph J Gitomer

(74) *Attorney, Agent, or Firm* — Dinsmore & Shohl LLP

(57) ABSTRACT

Methods of treating a methicillin-resistant *Staphylococcus aureus* (MRSA) infection or a *Staphylococcus pseudintermedius* infection in subject in need thereof are provided, the methods comprising administering to the subject an effective amount of a topical gel composition comprising vitamin E d-alpha-tocopherol polyethylene glycol 1000 succinate (TPGS); and at least one lipophile. Compositions, methods of manufacture, and methods of use in inhibiting microbial growth are also provided.

13 Claims, 11 Drawing Sheets

Determination of MIC & MBC of Topical Gel vs Mupirocin

S. aureus MIC & MBC trials

| | Gel | Mupirocin |
|---|---|---|
| MIC #1 | 2% | 1% |
| MIC #2 | 2% | 1% |
| MIC #3 | 3% | 1% |
| MBC #1 | 7% | 1% |
| MBC #2 | 7% | 1% |
| MBC #3 | 6% | 1% |

Fig. 4

TOPICAL GEL COMPOSITIONS FOR THE TREATMENT OF *STAPHYLOCOCCAL* INFECTIONS

CROSS REFERENCE TO RELATED APPLICATION

This application claims priority to U.S. Provisional Application Ser. No. 62/672,608, filed May 17, 2018, which is incorporated herein by reference in its entirety.

TECHNICAL FIELD

This disclosure relates to the field of skincare compositions and their methods of use. More specifically, this disclosure relates to topical skincare compositions useful for the treatment of disrupted skin conditions, including *Staphylococcus aureus* and *Staphylococcus pseudintermedius* infections.

BACKGROUND

A significant portion of breast cancer patients who undergo radiation treatment experience disrupted skin that can endure anywhere from a matter of weeks to, in the case of some patients, years after cessation of radiation treatment. Other skin conditions and disruptions exist in both humans and other mammals that have proven intractable to conventional treatment, or that require such frequent application of therapeutic ointment/lotions that the treatment itself becomes aversive.

Of particular concern are skin infections caused by antibiotic-resistant strains of bacteria, which are resistant to many conventional antibiotic agents and present a distinct challenge for management and treatment. Methicillin-resistant *Staphylococcus aureus* (MRSA) is a common resistant strain of bacteria affecting humans that does not respond to many antibiotics. In veterinary environments, methicillin-resistant *Staphylococcus pseudintermedius* (MRSP) is resistant strain of bacteria that can cause opportunistic infections in damaged skin, such as lick granulomas, particularly in dogs.

Skin treating formulations that may be used frequently by the patient and which provide both a positive, soothing subjective feel, as well as antibacterial and antioxidant effects, represent a continuing need in the art.

SUMMARY

Accordingly, provided herein is a method of treating a methicillin-resistant *Staphylococcus aureus* (MRSA) infection in a subject in need thereof, the method comprising administering to the subject an effective amount of a topical gel composition comprising: vitamin E d-alpha-tocopherol polyethylene glycol 1000 succinate (TPGS); and at least one lipophile.

In another embodiment, a method of treating a *Staphylococcus pseudintermedius* infection in a subject in need thereof is provided, the method comprising administering to the subject an effective amount of a topical gel composition comprising: vitamin E d-alpha-tocopherol polyethylene glycol 1000 succinate (TPGS); and at least one lipophile.

In another embodiment, a topical gel composition is provided, comprising: from about 17% to about 70% (w/w) vitamin E TPGS; and from about 1.7% to about 7% (w/w) of at least one lipophile selected from the group consisting of lavender oil, squalene oil, grapeseed oil, canola oil, saturated and unsaturated C8-C22 fatty acids, essential oils, fatty vegetable oils, and combinations thereof.

These and other objects, features, embodiments, and advantages will become apparent to those of ordinary skill in the art from a reading of the following detailed description and the appended claims.

BRIEF DESCRIPTION OF THE DRAWINGS

FIG. 4 is a table showing efficacy of topical gel vs. Mupirocin against *S. aureus*, as demonstrated by Minimum Inhibitory Concentrations (MIC) and Minimum Bactericidal Concentrations (MBC). Bacteria were inoculated ($\sim 1\times10^6$-$1\times10^7$ cells/ml) into varying concentrations (0, 1, 2, 3, 4, 5, 6, 7, 8, 9, 10% w/v) of topical gel or Mupirocin and incubated overnight at 37° C. MIC was determined by visually observing where turbid growth stopped, MBC was determined by taking aliquots from each tube, plating onto media, and observation for lack of any growth. Although Mupirocin showed lower MBC values compared to topical gel, with respect to MIC, results show topical gel was within a 1%-1.3% range compared to Mupirocin.

DETAILED DESCRIPTION

Figure 1:
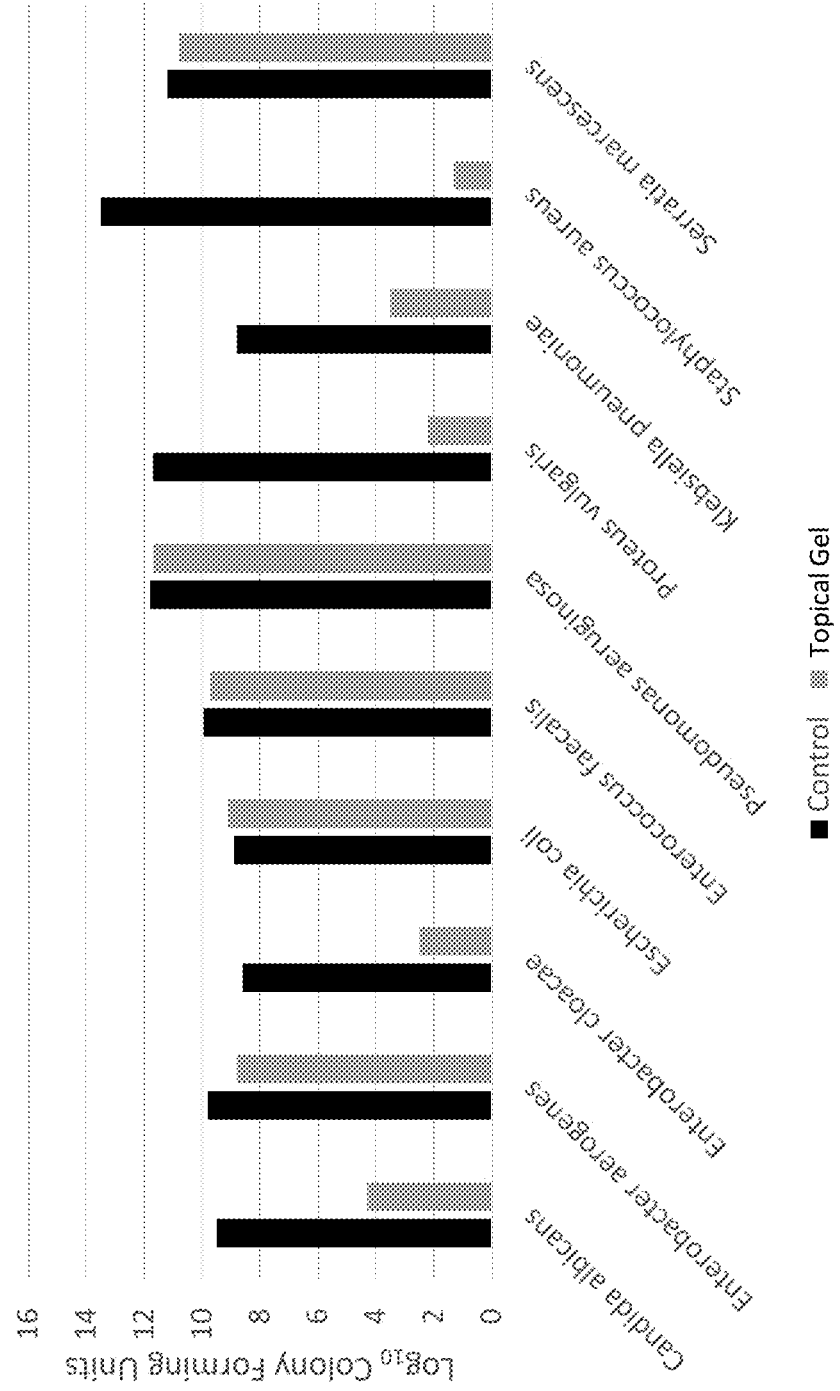
FIG. 1 depicts the viability of various microorganisms treated with 4% topical gel. Microorganisms were inoculated ($\sim 1\times10^6$-$1\times10^7$ cells/ml) in either LB broth (control) or LB broth+4% topical gel, incubated overnight at 37° C. with shaking, and serially diluted and plated on LB agar. CFUs were counted at 24-48 hrs growth. Results show the topical gel has marked efficacy against *Staphylococcus aureus*.

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The terms "treat," "treatment," and "treating," as used herein, refer to a method of alleviating or abrogating a disease, disorder, and/or symptoms thereof in a subject, including a mammal. In certain embodiments, the subject is a human subject. In certain embodiments, the subject is a veterinary subject, including dogs, cats, cattle, and other primates.

Unless otherwise specified, all percentages and amounts expressed herein and elsewhere in the disclosure should be understood to refer to percentages by weight, based on total weight of the composition (w/w %).

Topical Gel Compositions

Accordingly, embodiments of the disclosure are directed to antioxidant and antimicrobial compositions formulated for application to the skin and methods of use and manufacture of the same. Components are combined and blended in a sequential manner to obtain a clear gel exhibiting antimicrobial and antioxidant efficacy against a variety of bacteria, including methicillin-resistant bacteria. The topical gel compositions further provide therapeutic effect against a variety of disrupted skin conditions.

In one embodiment, provided herein is a topical gel comprising vitamin E d-alpha-tocopherol polyethylene glycol 1000 succinate (TPGS); and at least one lipophile.

Vitamin E TPGS ("TPGS") is formed by the esterification of vitamin E succinate with polyethylene glycol 1000. As a nonionic surfactant, TPGS exhibits amphipathic properties and can form stable micelles in aqueous vehicles at concentrations as low as 0.02 wt %. TPGS is available from a variety of sources, including Antares Health Products, Jonesborough, Tenn. TPGS is a waxy solid at room temperature, which can be melted and mixed with a lipophile according to the present disclosure to create a topical gel for application to the skin or other surfaces.

In embodiments, the topical gel composition comprises (w/w %) from about 17% to about 70% TPGS; from about 17% to about 51% TPGS; from about 17% to about 34% TPGS; from about 34% to about 70% TPGS; from about 34% to about 51% TPGS; or from about 51% to about 70% TPGS. In a more specific embodiment, the topical gel composition comprises about 17%, about 34%, about 51%, about 69.8%, or about 70% (w/w) TPGS.

Various lipophiles are suitable for use in the topical gel compositions of the present disclosure. In embodiments, the lipophile is selected from the group consisting of lavender oil, squalene oil, grapeseed oil, canola oil, saturated and unsaturated C8-C22 fatty acids, essential oils, fatty vegetable oils, and combinations thereof. In a specific embodiment, the lipophile is lavender oil (*Lavandula angustifolia*), and is available from a variety of sources, including New Directions Aromatics, Mississauga, Ontario, Canada.

Squalene oil is a natural organic compound obtained from shark liver oil or a variety of plant sources. Squalene is a precursor for synthesis of plant and animal sterols and plays a role in skin lubrication and protection. Grapeseed oil is pressed from the seeds of grapes and is a by-product of wine-making processes. Canola is a vegetable oil derived from a variety of rapeseed that is low in erucic acid. C8-C22 fatty acids include fatty acids having a saturated or unsaturated carbon chain of 8-22 carbon atoms. Suitable C8-C22 fatty acids include, but are not limited to, caprylic acid, capric acid, lauric acid, myristic acid, palmitic acid, stearic acid, arachidic acid, behenic acid, myristoleic acid, plamitoleic acid, sapienic acid, oleic acid, elaidic acid, vaccenic acid, linoleic acid, linoelaidic acid, alpha-linoleic acid, arachidonic acid, and the like, and combinations thereof.

Essential oils are concentrated hydrophobic liquids containing volatile compounds of the plants from which they are extracted. Such oils are essential, in that they contain the essence of the plant's characteristic fragrance. Non-limiting examples of suitable essential oils include sweet orange, peppermint, cedarwood, lemon, *eucalyptus*, clove, rosemary, lavender, frankincense, sage, cypress, fennel, ginger, lemongrass, mandarin, tea tree, grapefruit, rose, and the like, and combinations thereof. Essential oils are available from a variety of commercial sources.

Fatty vegetable oils are triglyceride vegetable oils obtained from various plant sources. Suitable fatty vegetable oils include, but are not limited to, palm oil, soybean oil, rapeseed oil, sunflower seed oil, canola oil, peanut oil, cottonseed oil, palm kernel oil, coconut oil, olive oil, corn oil, grapeseed oil, hazelnut oil, linseed oil, safflower oil, sesame oil, brazil nut oil, avocado oil, hemp seed oil, and the like, and combinations thereof.

In embodiments, the topical gel composition comprises from about 1.7% to about 7% lipophile; from about 1.7% to about 5.1% lipophile; from about 1.7% to about 3.4% lipophile; from about 3.4% to about 7% lipophile; from about 3.4% to about 5.1% lipophile; or from about 5.1% to about 7% lipophile. In a more specific embodiment, the topical gel composition comprises about 1.7%, about 3.4%, about 5.1%, or about 7% lipophile.

In embodiments, the topical gel composition comprises water, and more specifically, deionized distilled water. The ratio of TPGS/water/lipophile defines the consistency and viscosity of the gel and can be adjusted by the skilled artisan to achieve the viscosity of interest. In embodiments, the composition comprises from about 18% to about 80% water; from about 18% to about 60% water; from about 18% to about 40% water; from about 40% to about 80% water; from about 40% to about 60% water; from about 60% to about 80% water. In a more specific embodiment, the topical gel composition comprises about 18%, about 40%, about 60%, or about 80% water. The skilled artisan will appreciate that higher water concentration provides a less viscous gel suitable for application, for example, as a spray.

In embodiments, the topical gel composition comprises ascorbyl palmitate. Ascorbyl palmitate is an ester formed from ascorbic acid and palmitic acid, which is a fat-soluble form of vitamin C having antioxidant properties. In embodiments, the composition comprises from about 0.9% to about 3.6% ascorbyl palmitate; from about 0.9% to about 2.7% ascorbyl palmitate; from about 0.9% to about 1.8% ascorbyl palmitate; from about 1.8% to about 3.6% ascorbyl palmitate; from about 1.8% to about 2.7% ascorbyl palmitate; from about 2.7% to about 3.6% ascorbyl palmitate. In a more specific embodiment, the topical gel composition comprises about 0.9%, about 1.8%, 2.7%, or about 3.6% ascorbyl palmitate.

In embodiments, the topical gel composition comprises zinc aspartate. In a specific embodiment, the zinc aspartate is zinc-L-aspartate. Zinc aspartate is a salt of zinc and the amino acid aspartic acid. In embodiments, the composition comprises from about 0.4% to about 1.6% zinc aspartate; from about 0.4% to about 1.1% zinc aspartate; from about 0.4% to about 0.8% zinc aspartate; from about 0.8% to about 1.6% zinc aspartate; from about 0.8% to about 1.1% zinc aspartate; from about 1.1% to about 1.6% zinc aspartate. In a more specific embodiment, the topical gel composition comprises about 0.4%, about 0.8%, 1.1%, or about 1.6% zinc aspartate.

In embodiments, the topical gel optionally comprises an effective amount of lidocaine. A non-limiting example is lidocaine HCL, having the following structural formula:

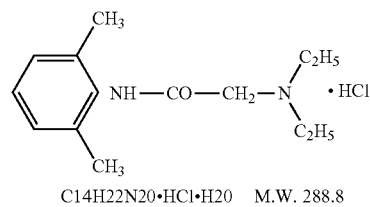

C14H22N20•HCl•H20   M.W. 288.8

In a specific embodiment, the topical gel composition comprises from about 17% to about 70% vitamin E TPGS; from about 1.7% to about 7% lipophile; from about 0.9% to about 3.6% ascorbyl palmitate; from about 0.4% to about 1.6% zinc-L-aspartate; and from about 18% to about 80% deionized distilled water.

In another specific embodiment, the topical gel composition comprises about 17% vitamin E TPGS; about 1.7% lipophile; about 0.9% ascorbyl palmitate; about 0.4% zinc-L-aspartate; and about 80% deionized distilled water.

In another specific embodiment, the topical gel composition comprises about 34% TPGS, about 3.4% lipophile, about 1.8% ascorbyl palmitate, about 0.8% zinc-L-aspartate, and about 60% deionized distilled water.

In another specific embodiment, the topical gel composition comprises about 51% vitamin E TPGS; about 5.1% lipophile; about 2.7% ascorbyl palmitate; about 1.1% zinc-L-aspartate; and about 40% deionized distilled water.

In another specific embodiment, the topical gel composition comprises about 70% vitamin E TPGS; about 7% lipophile; about 3.6% ascorbyl palmitate; about 1.6% zinc-L-aspartate; and about 18% deionized distilled water.

Methods of Use

Any of the compositions disclosed herein are useful in treating disrupted skin conditions in human and animal subjects.

Disrupted skin conditions include, but are not limited to, skin disruptions associated with radiation therapy, wounds, burns, incisions, abrasions, insect bites, eczema, herpes (shingles and cold sores), lick granulomas, and "hots spots" caused by an animal licking an infected area.

An "effective amount," as used herein, refers to an amount of a topical gel composition that will decrease, reduce, inhibit, or otherwise abrogate microbial growth, including bacterial, fungal, and bacterial biofilm growth.

In one embodiment, a method of inhibiting microbial growth is provided, the method comprising applying to a treatment area an effective amount of a topical gel composition as described herein. In embodiments, the treatment area comprises a disrupted skin site of a subject, including a human or animal subject. In other embodiments, the treatment area comprises a hard surface of an appliance or prosthetic to be implanted in a subject, such as an artificial joint or dental implant. In embodiments, the microbial growth comprises growth of a microbe selected from the group consisting of *Candida albicans, Citrobacter freundii, Enterobacter aerogenes, Enterobacter doacae, Escherichia coli, Enterococcus faecalis, Pseudomonas aeruginosa, Proteus vulgaris, Klebsiella pneumoniae, Staphylococcus aureus, Serratia marcescens, Staphylococcus pseudintermedius*, MRSA, MRSP, and combinations thereof.

In a specific embodiment, a method of treating a methicillin-resistant *Staphylococcus aureus* (MRSA) infection in a subject in need thereof is provided, the method comprising administering to the subject an effective amount of a topical gel composition as described herein. In embodiments, the topical gel composition disrupts a bacterial cell membrane, thereby treating the MRSA infection. In embodiments, MRSA infection comprises a MRSA biofilm. In embodiments, the subject is a human or other mammal subject. In embodiments, the topical gel is applied to a target treatment area of the subject, where disrupted skin is present.

In another specific embodiment, a method of treating *Staphylococcus pseudintermedius* infection in a subject in need thereof is provided, the method comprising administering to the subject an effective amount of a topical gel composition as described herein. In embodiments, the topical gel composition disrupts a bacterial cell membrane, thereby treating the *S. pseudintermedius* infection. In embodiments, the *S. pseudintermedius* comprises methicillin-resistant *S. pseudintermedius* (MRSP). In embodiments, *S. pseudintermedius* infection comprises a *S. pseudintermedius* biofilm. In embodiments, the subject is selected from the group consisting of dogs, cats, cattle, and primates. In a very specific embodiment, the subject is a dog. In embodiments, the topical gel is applied to a target treatment area of the subject, where disrupted skin is present.

The topical gel compositions disclosed herein may vary in viscosity, according to the weight percentages of TPGS, lipophile, and water. More viscous compositions are suitable for topical application as a gel, applied as a thin layer to the targeted treatment area of the subject. Less viscous compositions are suitable for application as a thin layer to the targeted treatment area of the subject, as a spray applied to the targeted skin treatment area, or as a solution to spray or soak an appliance or prosthetic to decrease likelihood of infection once implanted in the subject.

These and other embodiments will be further understood in light of the following examples.

EXAMPLES

The following examples are given by way of illustration and are in no way intended to limit the scope of the present invention.

Example 1: Viability of Microorganisms Treated with 4% Topical Gel

To test the ability of the topical gel to inhibit microorganisms, a panel of Gram positive bacteria (*Staphylococcus*), Gram negative bacteria (*Enterobacter, Escherichia, Enterococcus, Pseudomonas, Proteus, Klebsiella*, and *Serratia*), and fungi (*Candida*) were assessed. Microorganisms were inoculated (~$1\times10^6$-$1\times10^7$ cells/ml) in either LB broth (control) or LB broth+4% (w/v) topical gel, incubated overnight at 37° C. with shaking, and serially diluted and plated on LB agar. Colony Forming Units (CFUs) were counted at 24-48 hrs growth. As shown in FIG. 1, the topical gel exhibits varying degrees of inhibition across the panel of microorganisms, and shows particular enhanced efficacy against *Staphylococcus aureus*.

Example 2: Effects of 8% Topical Gel on the Growth of *S. aureus* Over Time

Figure 2:
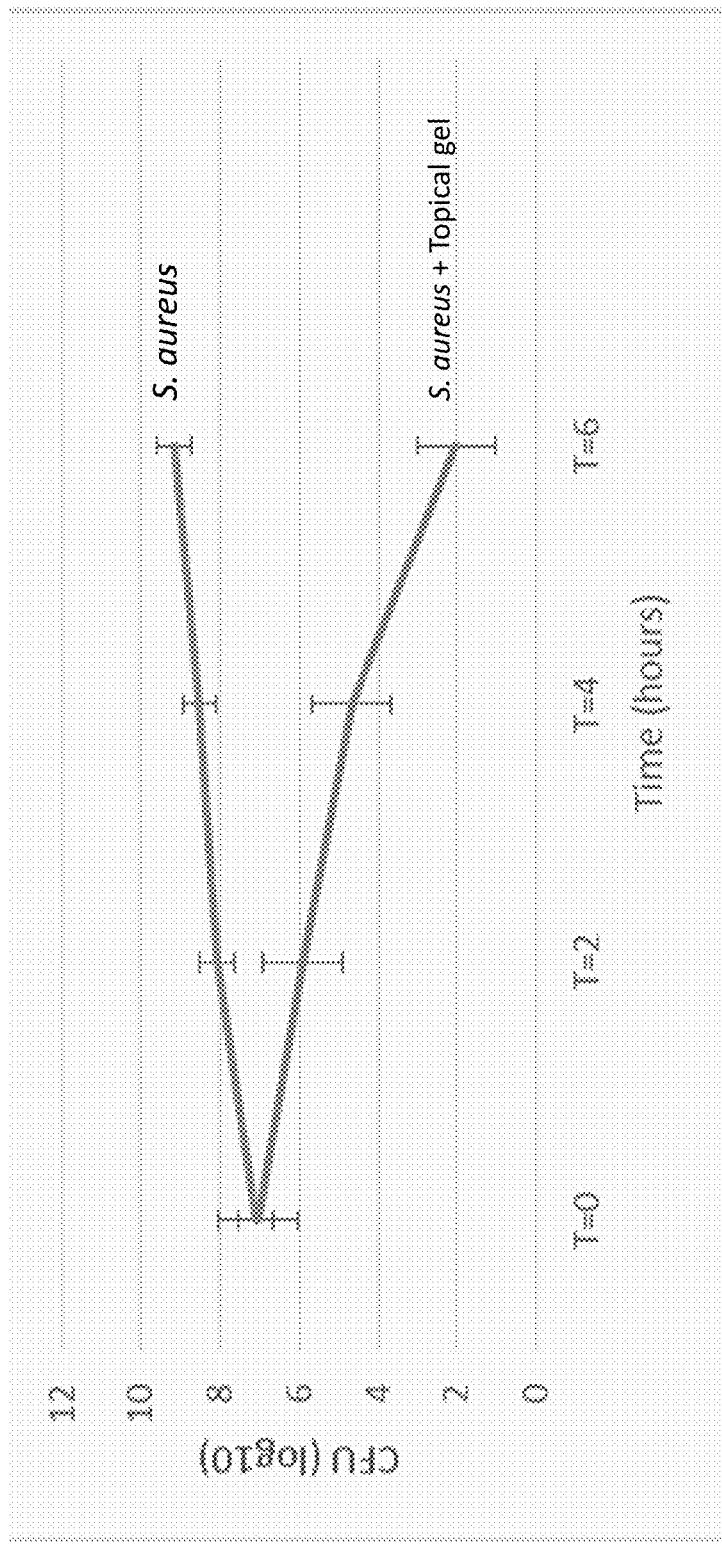
FIG. 2 depicts the effect of 8% topical gel on the growth of *S. aureus* over time. Bacteria were inoculated into LB broth (control) or LB broth+8% topical gel ($\sim 1\times10^6$-$1\times10^7$ cells/ml) and incubated at 37° C. with shaking. At time points of 0, 2, 4, and 6 hours post inoculation, an aliquot was taken, serially diluted, and plated on agar plates. CFUs were counted after 24-48 hrs. Results show the topical gel has an immediate inhibitory effect on *S. aureus* that continued over the time frame examined.

Bacteria were inoculated into LB broth (control) or LB broth+8% (w/v) topical gel (~$1\times10^6$-$1\times10^7$ cells/ml) and incubated at 37° C. with shaking. At time points of 0, 2, 4, and 6 hrs post inoculation, an aliquot was taken, serially diluted, and plated on LB agar plates. CFUs were counted after 24-48 hrs. As shown in FIG. 2, the topical gel has an immediate inhibitory effect on *S. aureus* that continued over the time frame examined.

Example 3: Effects of 8% Topical Gel on the Growth of MRSA

Figure 3:
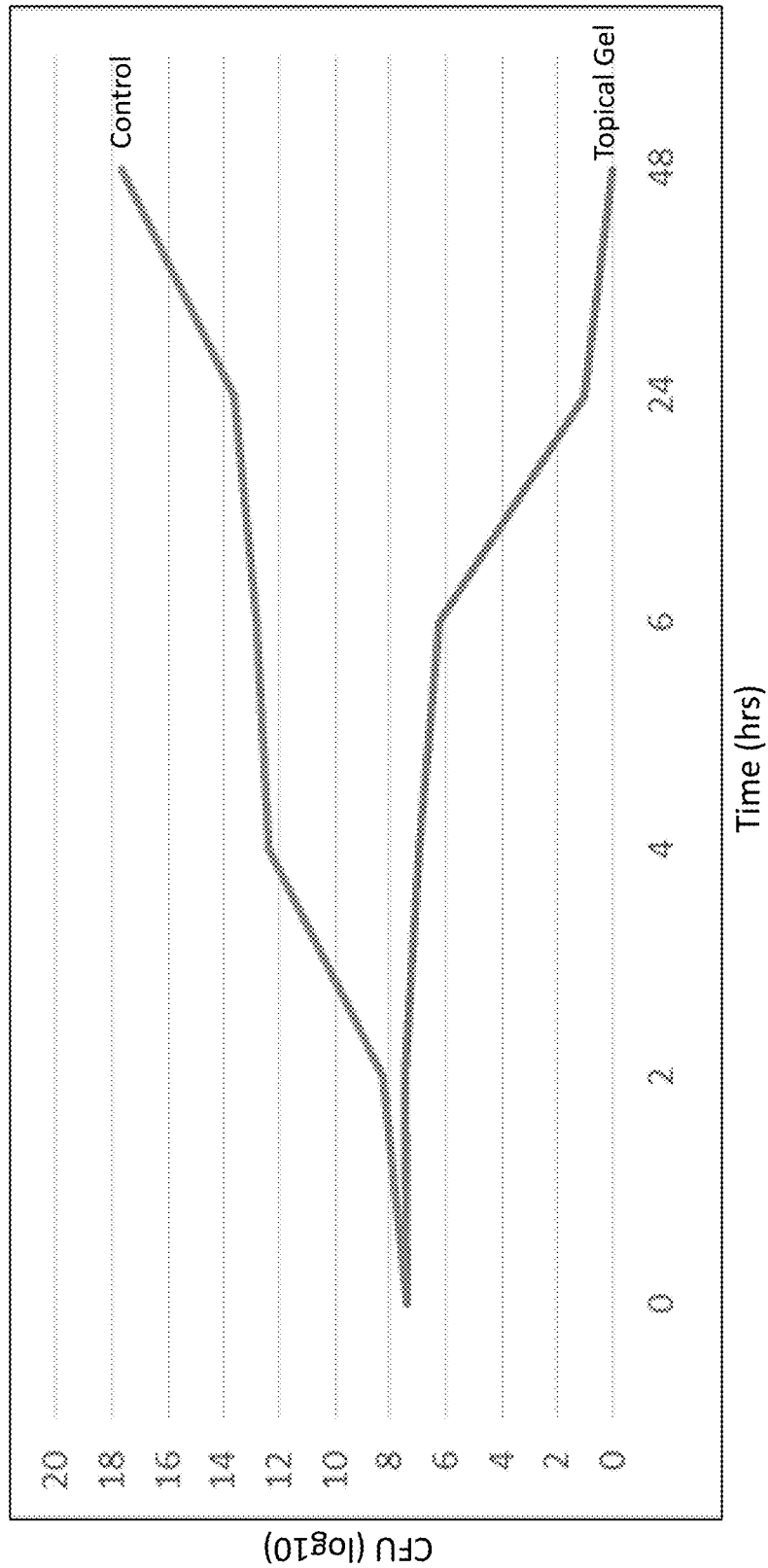
FIG. 3 depicts the effect of 8% topical gel on the growth of MRSA over time. Bacteria were inoculated into LB broth (control) or LB broth+8% topical gel ($\sim 1\times10^6$-$1\times10^7$ cells/ml) and incubated at 37° C. with shaking. At time points of 0, 2, 4, 6, 24, and 48 hours post inoculation, an aliquot was taken, serially diluted, and plated on agar plates. CFUs were counted after 24-48 hrs. Results show the topical gel has an immediate inhibitory effect on MRSA that continued over the time frame examined to near elimination by 48 hrs.

Bacteria were inoculated into LB broth (control) or LB broth+8% (w/v) topical gel (~$1\times10^6$-$1\times10^7$ cells/ml) and incubated at 37° C. with shaking. At time points of 0, 2, 4, 6, 24, and 48 hrs post inoculation, an aliquot was taken, serially diluted, and plated on agar plates. CFUs were counted after 24-48 hrs. As shown in FIG. 3, the topical gel has an immediate inhibitory effect on MRSA that continued over the time frame examined to near elimination by 48 hrs.

Example 4: Comparative Efficacy of Topical Gel Vs. Mupirocin Against *S. aureus*

Mupirocin is the standard ointment for treatment of *S. aureus* topical infections. To compare the MIC and MBC of the topical gel to that of Mupirocin, bacteria were inoculated (~$1\times10^6$-$1\times10^7$ cells/ml) into varying concentrations (0, 1, 2, 3, 4, 5, 6, 7, 8, 9, 10% w/v) of topical gel or Mupirocin and incubated overnight at 37° C. MIC was determined by visually observing where turbid growth stopped, MBC was determined by taking aliquots from each tube, plating onto media, and observation for lack of any growth. Results are shown in FIG. 4. Although Mupirocin showed lower MBC values compared to topical gel, with respect to MIC, results show the topical gel MIC values were surprisingly within 1%-1.3% of MIC values for Mupirocin.

Figure 5:
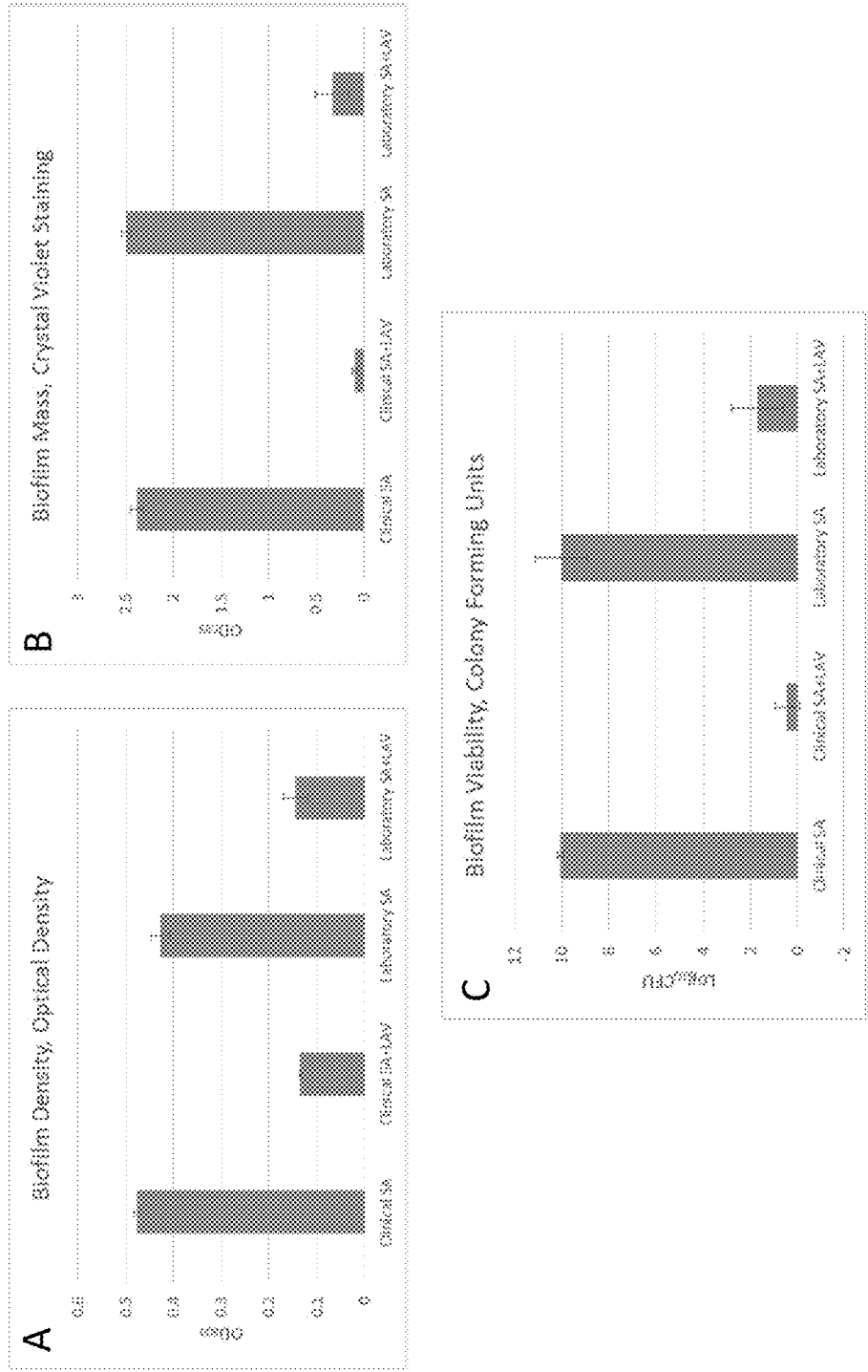
FIG. 5 depicts efficacy of topical gel during the attachment phase of biofilm development for clinical or laboratory strains of *S. aureus*. Bacteria were inoculated ($\sim 1\times10^6$-$1\times10^7$ cells/ml) at the same time as application of 8% topical gel and incubated overnight at 37° C. (A) Optical density (turbidity), (B) biofilm mass (crystal violet staining), and (C) biofilm viability (CFU) of remaining cells were tested. Results show the topical gel inhibits density, mass, and viability of *S. aureus* biofilms during the attachment phase.
Figure 6:
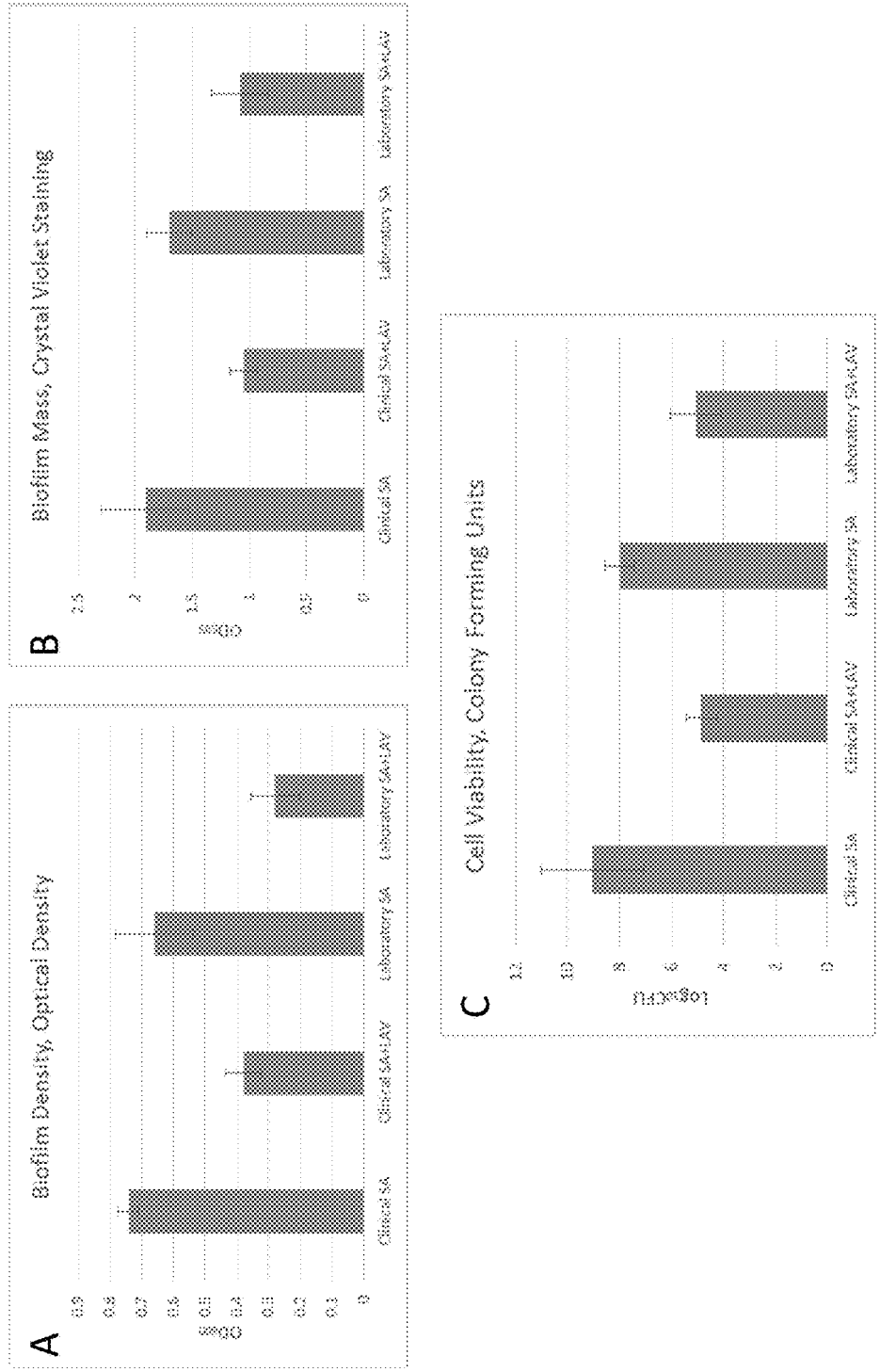
FIG. 6 depicts efficacy of topical gel during the maturation phase of biofilm development for clinical or laboratory strains of *S. aureus*. Bacteria were inoculated ($\sim 1\times10^6$-$1\times10^7$ cells/ml) and 8% topical gel was added after the biofilms were allowed to grow uninhibited for 24 hrs. (A) Optical density (turbidity), (B) biofilm mass (crystal violet staining), and (C) biofilm viability (CFU) of remaining cells were tested. Results show the topical gel inhibits density, mass, and viability of *S. aureus* biofilms during the maturation phase.
Figure 7:
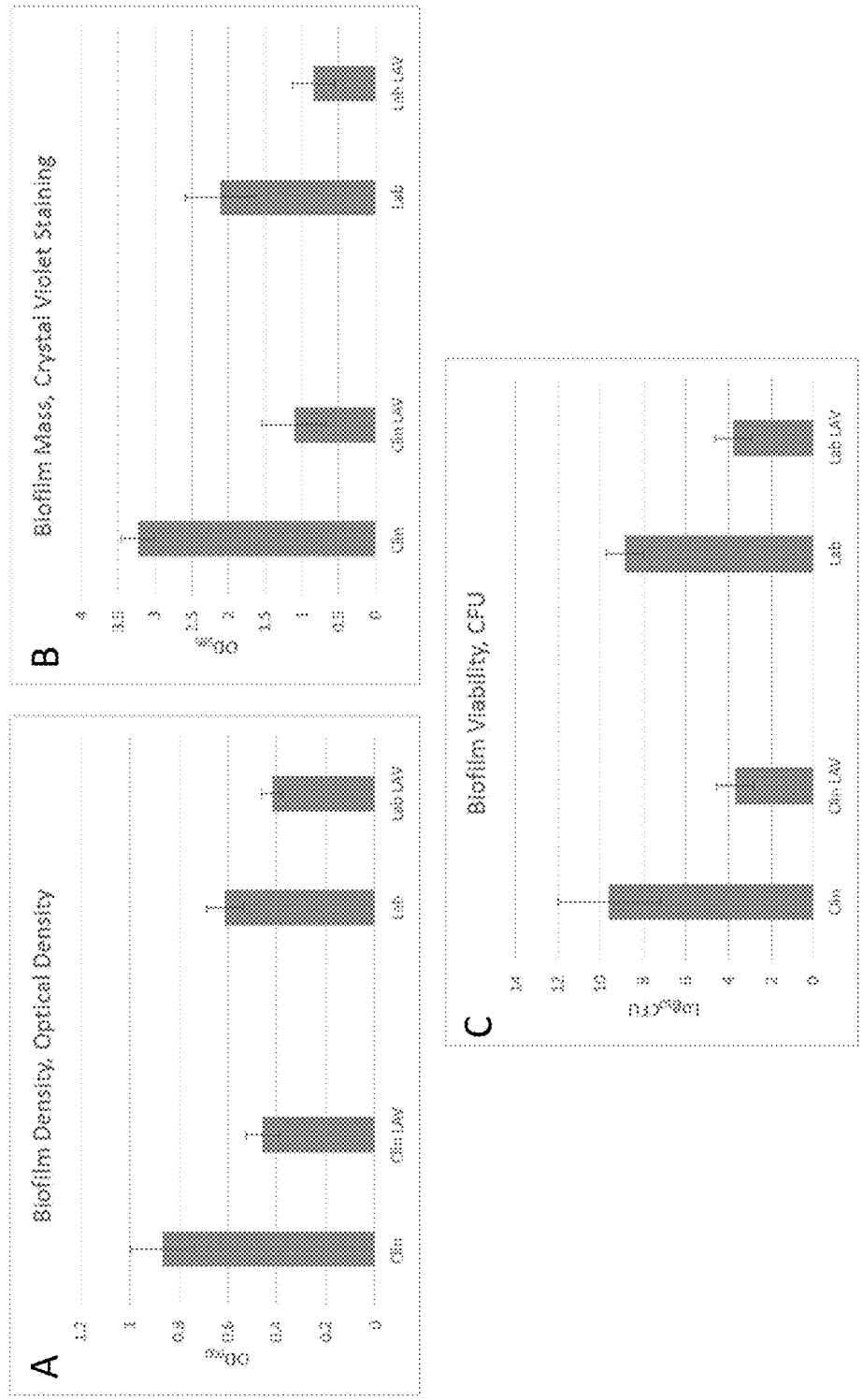
FIG. 7 shows efficacy of topical gel during the dispersion phase of biofilm development for clinical or laboratory strains of S. aureus. 8% topical gel was applied to a 48 hr preformed biofilm. (A) Optical density (turbidity), (B) biofilm mass (crystal violet staining), and (C) biofilm viability (CFU) of remaining cells were tested. Results show the topical gel inhibits density, mass, and viability of S. aureus biofilms during the dispersion phase.

Example 5: Determination of MIC and MBC of Topical Gel Vs. Mupirocin on *S. aureus* Biofilms Inhibitory efficacy of the topical gel was assessed against static *S. aureus* biofilms, which are harder to eradicate, particularly over the three phases of biofilm development. In the attachment phase, bacteria were inoculated (~$1\times10^6$-$1\times10^7$ cells/ml) at the same time as application of 8% (w/v) topical gel and incubated overnight at 37° C. Optical density (via measurement of turbidity), bacterial mass (via crystal violet staining), and viability (via CFU counts) of remaining cells were enumerated. Results are shown in FIG. 5 (A)-(C). In the maturation phase, the 8% (w/v) topical gel was added after the biofilms were allowed to grow uninhibited for 24 hours to determine if topical gel could inhibit preformed biofilms. Optical density (via measurement of turbidity), bacterial mass (via crystal violet staining), and viability (via CFU counts) of remaining cells were enumerated. Results are shown in FIG. 6 (A)-(C). In dispersion phase, 8% (w/v) topical gel was applied to a 48 hour preformed biofilm to determine inhibition of later biofilm events. Optical density (via measurement of turbidity), bacterial mass (via crystal violet staining), and viability (via CFU counts) of remaining cells were enumerated. Results are shown in FIG. 7 (A)-(C). In all three phases of biofilm development, the topical gel inhibited density, biofilm mass, and viability of *S. aureus* biofilms.

Figure 8:
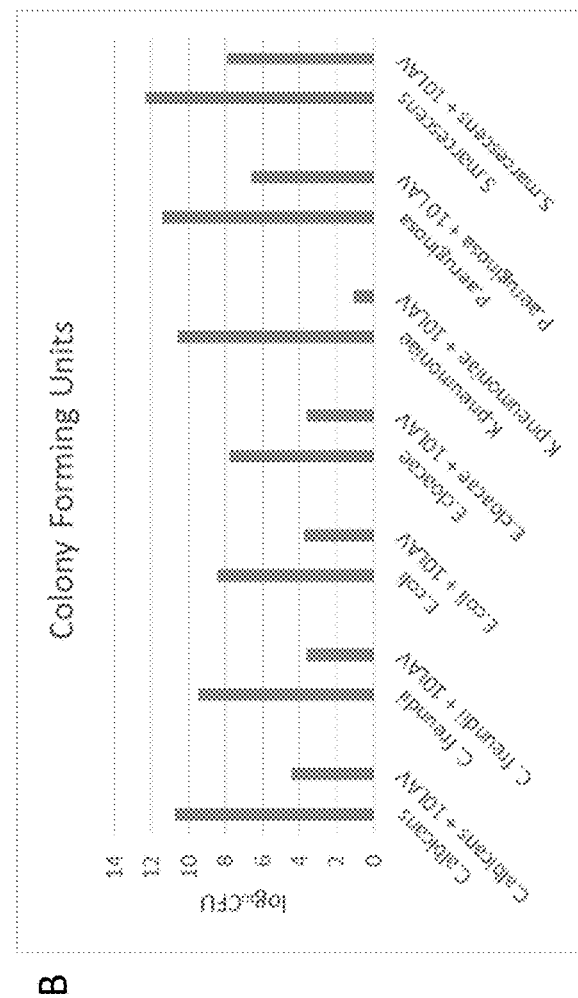
FIG. 8 shows MIC and MBC values for microorganisms treated with topical gel. Bacteria were inoculated (~1×10$^6$-1×10$^7$ cells/ml) into varying concentrations (0, 1, 2, 3, 4, 5, 6, 7, 8, 9, 10% w/v) of topical gel (LAV) and incubated overnight at 37° C. (A) MIC was determined by visually observing where turbid growth stopped, MBC was determined by taking aliquots from each tube, plating onto media, and observation for lack of any growth. (B) shows CFUs for control vs. 10% LAV for each strain of bacteria. Results show the topical gel appears to be bacteriostatic (as opposed to cidal) against the tested bacteria.

Example 6—Topical Gel Shows Bacteriostatic Effect Against Panel of Microorganisms MIC and MBC values were determined for microbes that showed the greatest inhibition by topical gel. Bacteria were inoculated (~$1 \times 10^6$-$1 \times 10^7$ cells/ml) into varying concentrations (0, 1, 2, 3, 4, 5, 6, 7, 8, 9, 10% w/v) of topical gel (LAV) and incubated overnight at 37° C. MIC was determined by visually observing where turbid growth stopped, MBC was determined by taking aliquots from each tube, plating onto media, and observation for lack of any growth. Results are shown in FIG. 8(A)-(B). Results suggest the topical gel functions in a bacteriostatic manner (as opposed to a bactericidal manner) against the tested bacteria.

Figure 9:
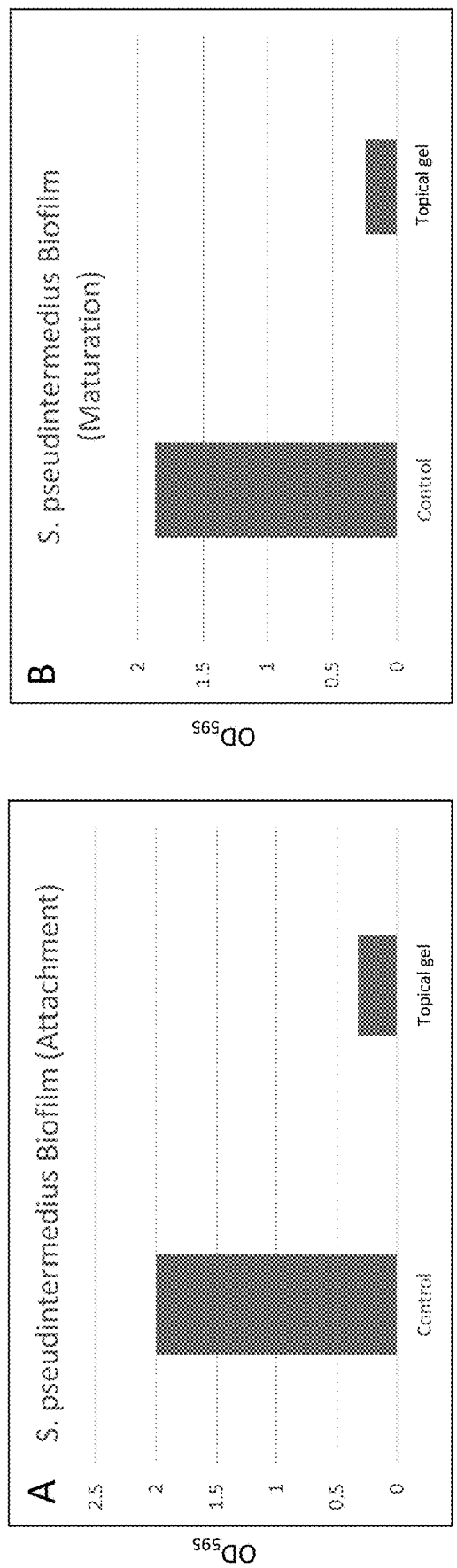
FIG. 9 shows efficacy of the topical gel during the attachment and maturation phases of biofilm development of S. pseudintermedius. (A) In the attachment phase, bacteria were inoculated (~1×10$^6$-1×10$^7$ cells/ml) at the same time as application of 8% topical gel and incubated overnight at 37° C. (B) In the maturation phase, the 8% topical gel was added after the biofilms were allowed to grow uninhibited for 24 hrs. Bacterial mass was calculated by crystal violet staining. Results show the topical gel inhibits mass of S. pseudintermedius biofilms

Example 7—Topical Gel is Effective Against *S. pseudintermedius* Biofilm Mass Efficacy of the topical gel was assessed during the attachment and maturation phases of *S. pseudintermedius* biofilms. In the attachment phase, bacteria were inoculated (~$1 \times 10^6$-$1 \times 10^7$ cells/ml) at the same time as application of 8% (w/v) topical gel and incubated overnight at 37° C. In the maturation phase, the 8% (w/v) topical gel was added after the biofilms were allowed to grow uninhibited for 24 hrs. Bacterial mass was calculated by crystal violet staining. As shown in FIG. 9(A)-(B), the topical gel inhibited mass of *S. pseudintermedius* biofilms during both the attachment and maturation phases.

Example 8—Effect of Topical Gel on *S. aureus* Gene Expression

Figure 10:
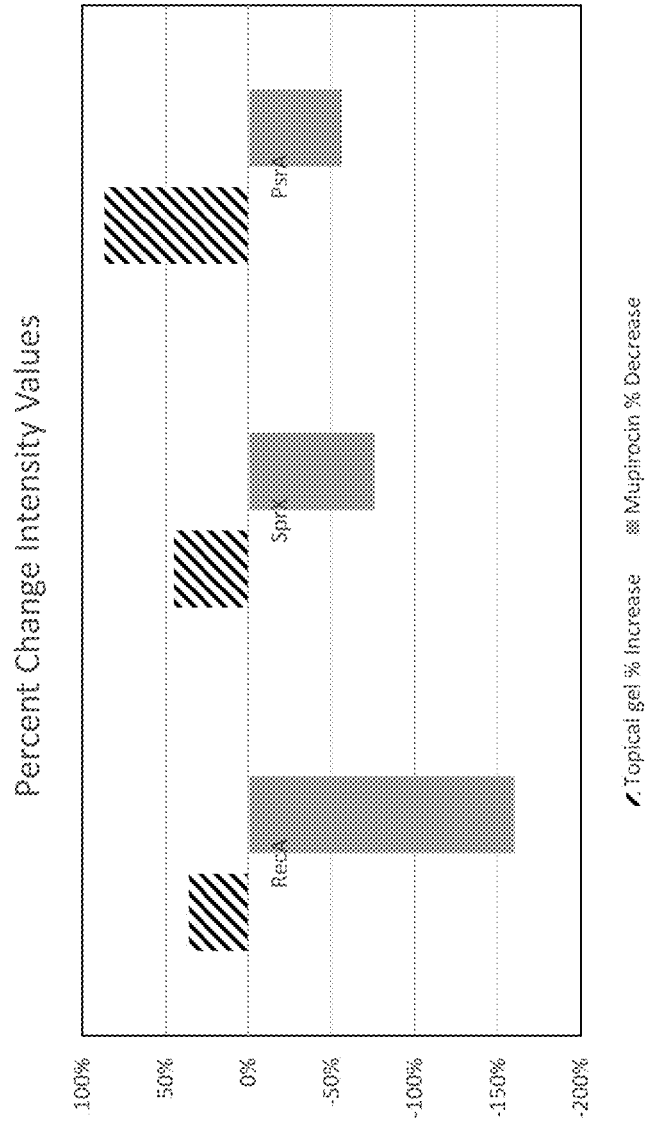
FIG. 10 is a graph showing the effect of the topical gel on S. aureus gene expression compared to mupirocin treatment. Results are expressed as percent change in intensity values.
Figure 11:
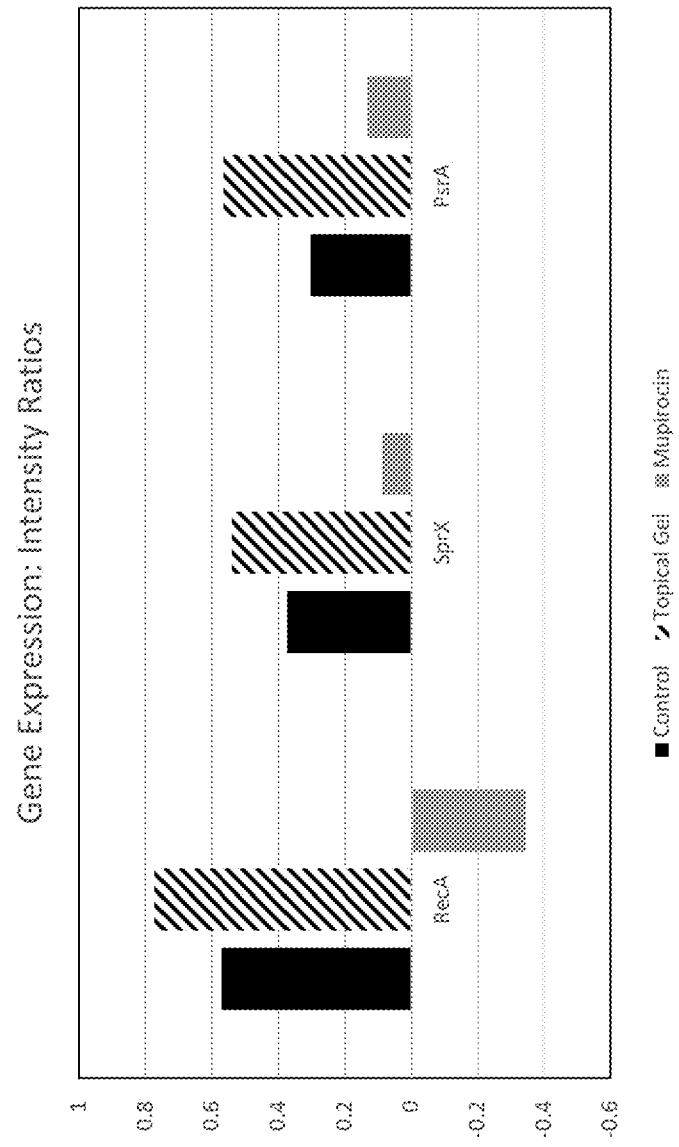
FIG. 11 is a graph showing the effect of the topical gel on S. aureus gene expression compared to control and mupirocin treatment. Results are expressed as gene expression intensity ratios.

In an effort to elucidate the mechanism of action of the topical gel on *S. aureus* as well as to examine any commonalities or differences in Staphylococcal response to treatment, transcriptional response was evaluated. *S. aureus* was either 1) grown alone as a control, 2) grown in 1% (w/v) topical gel, or 3) grown in 1% (w/v) Mupirocin for one hour. Cells were harvested and total RNA was extracted. Reverse Transcriptase polymerase chain reaction using gene specific primers was utilized to determine the RNA levels for the specific genes RecA, SprX, and PsrA. RecA is a protein specific for SOS response in *Staphylococcus* indicative of a need to repair DNA damage. SprX is a small RNA associated with *Staphylococcus* antibiotic resistance. PsrA regulates expression of proteins in the cell wall of *Staphylococcus* which are both essential for bacterial survival and antibiotic resistance. As shown in FIGS. 10-11, the topical gel induced a 36% increase in expression of RecA compared to controls, while Mupirocin reduced expression 160%. Expression levels of SprX were induced 45% by the topical gel, while Mupirocin reduced expression 78%. The topical gel induced PsrA expression by 87%, while Mupirocin reduced expression 56%. This preliminary data demonstrates that the topical gel works in a different manner than Mupirocin when *Staphylococcus* is exposed to the different treatment options.

Example 9—Exemplary Formulations

Exemplary topical gel formulations of varying viscosity are prepared as follows:

| | Topical Gel Lab Formula | | | |
|---|---|---|---|---|
| | 18% Water | 40% Water | 60% Water | 80% Water |
| | g | g | g | g |
| Vitamin E TPGS (TPGS) | 270 | 270 | 270 | 270 |
| Deionized Distilled Water (DDW) | 70 | 211 | 475 | 1268 |
| Lipophile (Lavender Oil) | 27 | 27 | 27 | 27 |
| Ascorbyl Palmitate | 14 | 14 | 14 | 14 |
| Zinc-L-aspartate | 6 | 6 | 6 | 6 |
| | 387 | 528 | 792 | 1585 |
| | (w/w %) | (w/w %) | (w/w %) | (w/w %) |
| (%) TPGS (g/100 g) | 69.8 | 51.1 | 34.1 | 17.0 |
| (%) DDW (g/100 g) | 18.1 | 40.0 | 60.0 | 80.0 |
| (%) Lipophile (Lavender oil) (g/100 g) | 7.0 | 5.1 | 3.4 | 1.7 |
| (%) Ascorbyl Palmitate (g/100 g) | 3.6 | 2.7 | 1.8 | 0.9 |
| (%) Zinc-L-Aspartate (g/100 g) | 1.6 | 1.1 | 0.8 | 0.4 |

The lipophile in exemplary formulations is lavender oil, which also functions as an analgesic agent. A lipophile is necessary for the manufacture of a gel; non-limiting exemplary substitute lipophiles include squalene oil, grapeseed oil, canola oil, saturated and unsaturated C8-C22 fatty acids, essential oils, fatty vegetable oil, or combinations thereof in the same amount/concentration as lavender oil. All of these formulations exhibit substantially the same antimicrobial activity against *S. aureus* and MRSA.

The ratio of TPGS/water/lipophile defines the consistency and viscosity of the gel.

Formulations according to the disclosure provide a moisture balance as an aspect to a therapeutic benefit when applied to skin.

Example 10—Process for Manufacture of Topical Gel

Preparation of Starting Materials
1. Ascorbyl palmitate is ground to a fine powder to reduce particle size prior to being added to the blend.
2. Zinc-L-aspartate is ground to a fine powder to reduce particle size prior to being added to the blend.
3. Vitamin E-TPGS (a wax at room temperature) is cut into large chunks, placed into large receptacle (600 ml or greater), covered with aluminum foil and put in an incubator oven at 60° C. until melted into a clear, golden-colored viscous liquid. Preparation of liquid vitamin E-TPGS should be done within three days of use in manufacturing the topical gel.

Preparation of Topical Gel
This process of manufacture is suitable for use in manufacturing any of the formulations disclosed herein.

1. Transfer vitamin E-TPGS (melted liquid) to a receptacle and heat to 70° C., under stirring conditions (Cole-Parmer Variable Speed Overhead Mixer fitted with an impeller on the end of the shaft, about 800 rpm).
2. Gradually add ascorbyl palmitate to the mixture while stirring at about 800 rpm.
3. Gradually add zinc-L-aspartate to the mixture while stirring at about 800 rpm.
4. Gradually add the selected lipophile to the receptacle. Continue stirring until a solution is formed.
5. Gradually add deionized distilled water (heated to 70 C) to the mixture and increase stirring speed to 1500 rpm.
6. Continue stirring at about 1500 rpm for 5 minutes or until a homogenous blend of all components is achieved. Ensure components are distributed evenly throughout the gel by changing the position of the impeller from the top to bottom of the solution. Once a homogenous gel is achieved, remove from the hot plate and allow gel to cool to room temperature.

Where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of treating a *Staphylococcus* infection in a subject in need thereof, the method comprising administering to the subject an effective amount of a topical gel composition comprising:
   from about 17% to about 70% (w/w) vitamin E d-alpha-tocopherol polyethylene glycol 1000 succinate (TPGS); and
   from about 1.7% to about 7% (w/w) of a lipophile,
   wherein the *Staphylococcus* is selected from the group consisting of *Staphylococcus aureus*, methicillin-resistant *Staphylococcus aureus* (MRSA), *Staphylococcus pseudintermedius*, methicillin-resistant *Staphylococcus pseudintermedius* (MRSP), and combinations thereof.

2. The method according to claim 1, wherein the lipophile is selected from the group consisting of lavender oil, squalene oil, grapeseed oil, canola oil, saturated and unsaturated C8-C22 fatty acids, essential oils, fatty vegetable oils, and combinations thereof.

3. The method according to claim 1, wherein the topical gel composition further comprises ascorbyl palmitate.

4. The method according to claim 1, wherein the topical gel composition further comprises zinc-L-aspartate.

5. The method according to claim 1, wherein the topical gel composition disrupts a bacterial cell membrane of the *Staphylococcus*, thereby treating the *Staphylococcus* infection.

6. The method according to claim 5, wherein the *Staphylococcus* infection comprises a biofilm.

7. The method according to claim 2, wherein the topical gel composition comprises:
   from about 17% to about 70% (w/w) vitamin E TPGS;
   from about 1.7% to about 7% (w/w) squalene oil or lavender oil;
   from about 0.9% to about 3.6% (w/w) ascorbyl palmitate;
   from about 0.4% to about 1.6% (w/w) zinc-L-aspartate; and
   from about 18% to about 80% (w/w) deionized distilled water.

8. The method according to claim 7, wherein the topical gel further comprises an effective amount of lidocaine.

9. The method according to claim 1, wherein the *Staphylococcus* is selected from the group consisting of *Staphylococcus pseudintermedius*, MRSP, and combinations thereof.

10. The method according to claim 9, wherein the subject is selected from the group consisting of dogs, cats, cattle, and primates.

11. The method according to claim 1, wherein the *Staphylococcus* is selected from the group consisting of *Staphylococcus aureus*, MRSA, and combinations thereof.

12. The method according to claim 11, wherein the subject is a mammal.

13. The method according to claim 12, wherein the subject is selected from the group consisting of humans, dogs, cats, and primates.

* * * * *